(12) United States Patent
Zones et al.

(10) Patent No.: US 7,422,732 B2
(45) Date of Patent: Sep. 9, 2008

(54) SYNTHESIS OF AMINES USING MOLECULAR SIEVE SSZ-74

(75) Inventors: Stacey I. Zones, San Francisco, CA (US); Allen W. Burton, Jr., Richmond, CA (US)

(73) Assignee: Chevron U.S.A. Inc, San Ramon, CA (US)

( * ) Notice: Subject to any disclaimer, the term of this patent is extended or adjusted under 35 U.S.C. 154(b) by 0 days.

(21) Appl. No.: 11/614,714

(22) Filed: Dec. 21, 2006

(65) Prior Publication Data

US 2007/0149819 A1    Jun. 28, 2007

Related U.S. Application Data

(60) Provisional application No. 60/754,866, filed on Dec. 28, 2005.

(51) Int. Cl.
| | |
|---|---|
| *C01B 33/36* | (2006.01) |
| *C01B 39/00* | (2006.01) |
| *C07C 209/00* | (2006.01) |
| *B01J 29/06* | (2006.01) |

(52) U.S. Cl. ............... 423/706; 423/328.1; 423/328.2; 423/329.1; 423/718; 564/474; 564/479; 502/64; 502/71

(58) Field of Classification Search .................. 423/706
See application file for complete search history.

(56) References Cited

U.S. PATENT DOCUMENTS

| | | | | |
|---|---|---|---|---|
| 4,537,757 A | * | 8/1985 | Chono et al. ................. 423/705 |
| 4,737,592 A | * | 4/1988 | Abrams et al. ............... 564/479 |
| 4,806,689 A | * | 2/1989 | Gier et al. .................... 564/474 |
| 4,814,503 A | * | 3/1989 | Abrams et al. ............... 564/474 |
| 4,874,896 A | * | 10/1989 | Olson et al. .................. 564/479 |
| 4,910,006 A | | 3/1990 | Zones et al. |
| 5,316,753 A | | 5/1994 | Nakagawa |
| 5,344,989 A | * | 9/1994 | Corbin et al. ................ 564/479 |

OTHER PUBLICATIONS

Flanigen, Edith M. Molecular Sieve Zeolite Technology—The First Twenty-five Years. Pure & Appl.Chem. Pergamon Press Ltd. 1980, vol. 52, pp. 2191-2211. http://www.iupac.org/publications/pac/1980/pdf/5209x2191.pdf.*

Flanigen, Edith M. Molecular Sieve Zeolite Technology—The First Twenty-five Years. Pure & Appl.Chem. Pergamon Press Ltd. 1980, vol. 52, pp. 2191-2211. http://www.iupac.org/publications/pac/1980/pdf/5209x2191.pdf.*

U.S. Appl. No. 11/614,670, filed Dec. 21, 2006, entitled Molecular Sieve SSZ-74 Composition of Matter and Synthesis Thereof, 20 pages.

U.S. Appl. No. 11/614,683, filed Dec. 21, 2006, entitled Hydrocarbon Conversion Using Molecular Sieve SSZ-74, 55 pages.

(Continued)

*Primary Examiner*—Jerry A. Lorengo
*Assistant Examiner*—Noah S Wiese
(74) *Attorney, Agent, or Firm*—Richard J. Sheridan; Susan M. Abernathy

(57) ABSTRACT

The present invention relates to new crystalline molecular sieve SSZ-74 prepared using a hexamethylene-1,6-bis-(N-methyl-N-pyrrolidinium)dication as a structure-directing agent, and its use in catalysts for synthesizing amines.

4 Claims, 1 Drawing Sheet

OTHER PUBLICATIONS

U.S. Appl. No. 11/614,688, filed Dec. 21, 2006, entitled Reduction of Oxides of Nitrogen in a Gas Stream Using Molecular Sieve SSZ-74, 18 pages.

U.S. Appl. No. 11/614,695, filed Dec. 21, 2006, entitled Partial Oxidation Using Molecular Sieve SSZ-74, 25 pages.

U.S. Appl. No. 11/614,701, filed Dec. 21, 2006, entitled Acylation Using Molecular Sieve SSZ-74, 18 pages.

U.S. Appl. No. 11/614,708, filed Dec. 21, 2006, entitled Oxygenate Conversion Using Molecular Sieve SSZ-74, 19 pages.

U.S. Appl. No. 11/614,638, filed Dec. 21, 2006, entitled Gas Separation Using Molecular Sieve SSZ-74, 17 pages.

U.S. Appl. No. 11/614,720, filed Dec. 21, 2006, entitled Treatment of Engine Exhaust Using Molecular Sieve SSZ-74, 25 pages.

U.S. Appl. No. 11/614,726, filed Dec. 21, 2006, entitled Beckmann Rearrangement Using Molecular Sieve SSZ-74, 22 pages.

* cited by examiner

SYNTHESIS OF AMINES USING MOLECULAR SIEVE SSZ-74

This application claims the benefit under 35 USC 119 of Provisional Application No. 60/754,866, filed Dec. 28, 2005.

BACKGROUND OF THE INVENTION

1. Field of the Invention

The present invention relates to new crystalline molecular sieve SSZ-74, a method for preparing SSZ-74 using a hexamethylene-1,6-bis(N-methyl-N-pyrrolidinium)dication as a structure directing agent ("SDA") and its use in the synthesis of amines.

2. State of the Art

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed) there is a continuing need for new molecular sieves. With desirable properties for gas separation and drying, hydrocarbon and chemical conversions, and other applications. New molecular sieves may contain novel internal pore architectures, providing enhanced selectivities in these processes.

SUMMARY OF THE INVENTION

In accordance with the present invention there is provided a process for producing methylamine or dimethylamine comprising reacting methanol, dimethyl ether or a mixture thereof and ammonia in the gaseous phase in the presence of a catalyst comprising a crystalline molecular sieve having a mole ratio greater than about 15 of (1) an oxide of a first tetravalent element to (2) an oxide of a trivalent element, pentavalent, element, second tetravalent element which is different from said first tetravalent element or mixture thereof and having, after calcination, the X-ray diffraction lines of Table II. It should be noted that the phrase "mole ratio greater than about 15" includes the case where there is no oxide (2), i.e., the mole ratio of oxide (1) to oxide (2) is infinity. In that case the molecular sieve is comprised of essentially all silicon oxide.

The present invention also provides such a process wherein the molecular sieve has a mole ratio greater than about 15 of (1) silicon oxide to (2) an oxide selected from aluminum oxide, gallium oxide, iron oxide, boron oxide, titanium oxide, indium oxide and mixtures thereof.

DETAILED DESCRIPTION OF THE INVENTION

Figure 1:
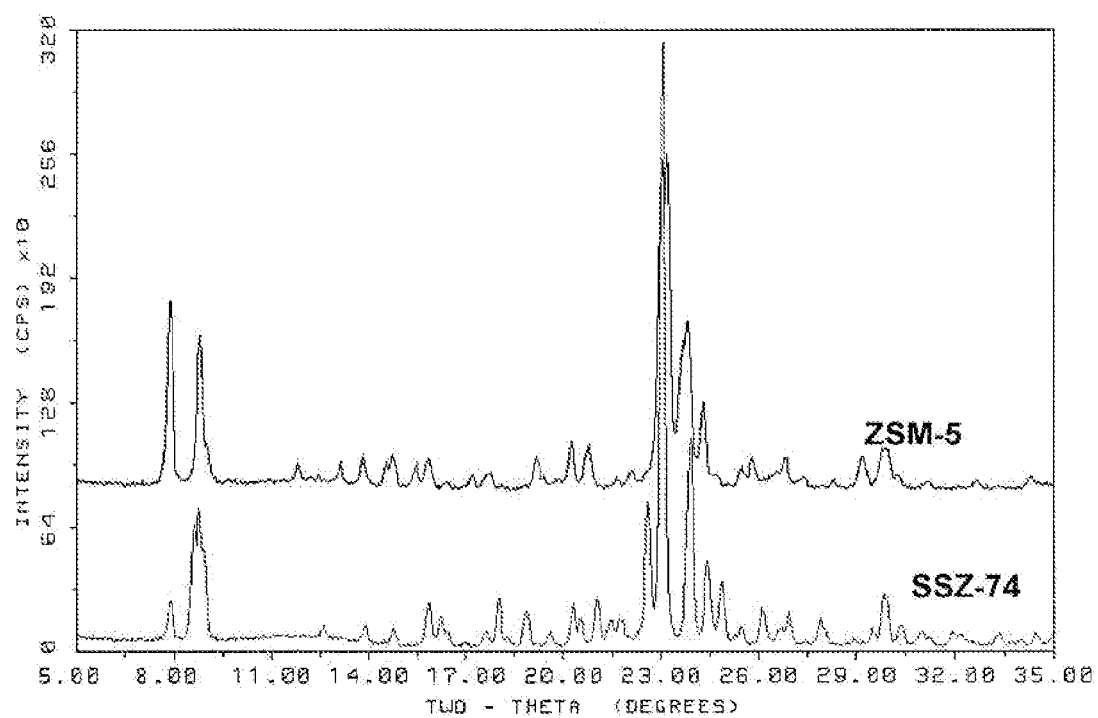
FIG. 1 shows a comparison of two X-ray diffraction patterns, the top one being ZSM-5 and the bottom one being SSZ-74.

The present invention comprises a molecular sieve designated herein "molecular sieve SSZ-74" or simply "SSZ-74".

In preparing SSZ-74, a hexamethylene-1,6-bis-(N-methyl-N-pyrrolidinium)dication is used as a structure directing agent ("SDA"), also known as a crystallization template. The SDA useful for making SSZ-74 has the following structure:

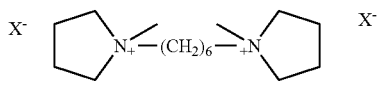

Hexamethylene-1,6-bis-(N-methyl-N-pyrrolidinium) dication

The SDA dication is associated with anions (X⁻) which may be any anion that is not detrimental to the formation of the SSZ-74. Representative anions include halogen, e.g., fluoride, chloride, bromide and iodide, hydroxide, acetate, sulfate, tetrafluoroborate, carboxylate, and the like. Hydroxide is the most preferred anion. The structure directing agent (SDA) may be used to provide hydroxide ion. Thus, it is beneficial to ion exchange, for example, a halide to hydroxide ion.

In general, SSZ-74 is prepared by contacting (1), an active source(s) of silicon oxide, and, optionally, (2) an active source(s) of aluminum oxide, gallium oxide, iron oxide, boron oxide, titanium oxide, indium oxide and mixtures thereof with the hexamethylene-1,6-bis-(N-methyl-N-pyrrolidinium)dication SDA in the presence of fluoride ion.

SSZ-74 is prepared from a reaction mixture comprising, in terms of mole ratios, the following:

TABLE A

| | Reaction Mixture | |
|---|---|---|
| | Typical | Preferred |
| $SiO_2/X_aO_b$ | 100 and greater | |
| $OH^-/SiO_2$ | 0.20–0.80 | 0.40–0.60 |
| $Q/SiO_2$ | 0.20–0.80 | 0.40–0.60 |
| $M_{2/n}/SiO_2$ | 0–0.04 | 0–0.025 |
| $H_2O/SiO_2$ | 2–10 | 3–1 |
| $HF/SiO_2$ | 0.20–0.80 | 0.30–0.60 | where X is aluminum, gallium, iron, boron, titanium, indium and mixtures thereof, a is 1 or 2, b is 2 when a is 1 (i.e., W is tetravalent); b is 3 when a is 2 (i.e., W is trivalent), M is an alkali metal cation, alkaline earth metal cation or mixtures thereof; n is the valence of M (i.e. 1 or 2); Q is a hexamethylene-1,6-bis-(N-methyl-N-pyrrolidinium) dication and F is fluoride.

As noted above, the $SiO_2/X_aO_b$ mole ratio in the reaction mixture is 100 and greater. This means that the $SiO_2/X_aO_b$ mole ratio can be infinity, i.e. there is no $X_aO_b$ in the reaction mixture. This results in a version of SSZ-74 that is essentially all silica. As used herein, "essentially all silicon oxide" or "essentially all-silica" means that the molecular sieve's crystal structure is comprised of only silicon oxide or is comprised of silicon oxide and only trace amounts of other oxides, such as aluminum oxide, which may be introduced as impurities in the source of silicon oxide.

A preferred source of silicon oxide is tetraethyl orthosilicate. A preferred source of aluminum oxide is LZ-210 zeolite (a type of Y zeolite).

In practices SSZ-74 is prepared by a process comprising:
(a) preparing an aqueous solution containing (1) a source(s) of silicon oxide, (2) a source(s) of aluminum oxide, gallium oxide, iron oxide, boron oxide, titanium oxide, indium oxide and mixtures thereof, (3) a source of fluoride ion and (4) a hexamethylene-1,6-bis-(N-methyl-N-pyrrolidinium)dication having an anionic counterion which is not detrimental to the formation of SSZ-74;
(b) maintaining the aqueous solution under conditions sufficient to form crystals of SSZ-74; and
(c) recovering the crystals of SSZ-74.

The reaction mixture is maintained at an elevated temperature until the crystals of the SSZ-74 are formed. The hydrothermal crystallization is usually conducted under autogenous pressure, at a temperature between 100° C. and 200°

C., preferably between 135° C. and 180° C. The crystallization period is typically greater than 1 day and preferably from about 3 days to about 20 days. The molecular sieve may be prepared using mild stirring or agitation.

During the hydrothermal crystallization step, the SSZ-74 crystals can be allowed to nucleate spontaneously from the reaction mixture. The use of SSZ-74 crystals as seed material can be advantageous in decreasing the time necessary for complete crystallization to occur. In addition, seeding can lead to an increased purity of the product obtained by promoting the nucleation and/or formation of SSZ-74 over any undesired phases. When used as seeds. SSZ-74 crystals are added in an amount between 0.1 and 10% of the weight of the first tetravalent element oxide; e.g. silica, used in the reaction mixture.

Once the molecular sieve crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized SSZ-74 crystals. The drying step can be performed at atmospheric pressure or under vacuum.

SSZ-74 as prepared has the X-ray diffraction lines of Table I below. SSZ-74 has a composition, as synthesized (i.e., prior to removal of the SDA from the SSZ-74) and in the anhydrous state, comprising the following (in terms of mole ratios):

| | |
|---|---|
| $SiO_2/X_cO_d$ | greater than 100 |
| $M_{2/n}/SiO_2$ | 0-0.03 |
| $Q/SiO_2$ | 0.30-0.70 |
| $F/SiO_2$ | 0.30-0.70 | wherein X is aluminum, gallium, iron, boron, titanium, indium and mixtures thereof, c is 1 or 2; d is 2 when c is 1 (i.e., W is tetravalent) or d is 3 or 5 when c is 2 (i.e., d is 3 when W is trivalent or 5 when W is pentavalent), M is an alkali metal cation, alkaline earth metal cation or mixtures thereof; n is the valence of M (i.e., 1 or 2); Q is a hexamethylene-1,6-bis-(N-methyl-N-pyrrolidinium)dication and F is fluoride.

SSZ-74 is characterized by its X-ray diffraction pattern. SS-74, as-synthesized, has a crystalline structure whose X-ray powder diffraction pattern exhibits the characteristic lines shown in Table I.

TABLE I

As-Synthesized SSZ-74

| 2 Theta[a] | d-spacing (Angstroms) | Relative Integrated Intensity (%)[b] |
|---|---|---|
| 7.95 | 11.11 | W |
| 8.68 | 10.18 | M |
| 8.85 | 9.98 | W-M |
| 9.02 | 9.80 | W |
| 22.69 | 3.92 | W-M |
| 23.14 | 3.84 | VS |
| 24.01 | 3.70 | M |
| 24.52 | 3.63 | W |
| 24.93 | 3.57 | W |
| 29.95 | 2.98 | W |

[a] ± 0.1
[b] The X-ray patterns provided are based on a relative intensity scale in which the strongest line in the X-ray pattern is assigned a value of 100: W (weak) is less than 20; M (medium) is between 20 and 40; S (strong) is between 40 and 60; VS (very strong) is greater than 60.

Table IA below shows the X-ray powder diffraction lines for as-synthesized SSZ-74 including actual relative intensities.

TABLE IA

As-Synthesized SSZ-74

| 2 Theta[a] | d-spacing (Angstroms) | Intensity |
|---|---|---|
| 7.95 | 11.11 | 7.9 |
| 8.68 | 10.18 | 21.1 |
| 8.85 | 9.98 | 18.7 |
| 9.02 | 9.80 | 11.3 |
| 11.30 | 7.82 | 0.4 |
| 12.70 | 6.96 | 1.8 |
| 13.98 | 6.33 | 2.4 |
| 14.77 | 5.99 | 0.5 |
| 14.85 | 5.96 | 2.1 |
| 15.93 | 5.56 | 6.3 |
| 16.30 | 5.43 | 4.6 |
| 16.50 | 5.37 | 1.8 |
| 17.05 | 5.20 | 0.8 |
| 17.41 | 5.09 | 0.1 |
| 17.71 | 5.00 | 2.0 |
| 18.09 | 4.90 | 7.4 |
| 18.38 | 4.82 | 0.7 |
| 18.89 | 4.69 | 0.9 |
| 18.96 | 4.68 | 4.4 |
| 19.69 | 4.51 | 1.8 |
| 20.39 | 4.35 | 5.1 |
| 20.63 | 4.30 | 4.2 |
| 21.12 | 4.20 | 7.7 |
| 21.55 | 4.12 | 5.4 |
| 21.75 | 4.08 | 0.5 |
| 21.80 | 4.07 | 1.4 |
| 21.88 | 4.06 | 2.1 |
| 21.96 | 4.04 | 1.5 |
| 22.17 | 4.01 | 0.8 |
| 22.69 | 3.92 | 18.9 |
| 23.14 | 3.84 | 100.0 |
| 23.89 | 3.72 | 9.4 |
| 24.01 | 3.70 | 25.6 |
| 24.52 | 3.63 | 13.7 |
| 24.68 | 3.60 | 2.1 |
| 24.93 | 3.57 | 11.3 |
| 25.09 | 3.55 | 0.9 |
| 25.37 | 3.51 | 1.7 |
| 25.57 | 3.48 | 2.7 |
| 26.20 | 3.40 | 5.5 |
| 26.31 | 3.38 | 0.8 |
| 26.67 | 3.34 | 2.0 |
| 26.76 | 3.33 | 1.0 |
| 26.82 | 3.32 | 0.9 |
| 27.01 | 3.30 | 3.4 |
| 27.05 | 3.29 | 0.8 |
| 27.48 | 3.24 | 0.8 |
| 27.99 | 3.19 | 4.2 |
| 28.18 | 3.16 | 0.8 |
| 28.78 | 3.10 | 0.6 |
| 29.03 | 3.07 | 0.7 |
| 29.31 | 3.04 | 0.9 |
| 29.58 | 3.02 | 2.4 |
| 29.95 | 2.98 | 9.6 |
| 30.44 | 2.93 | 3.7 |
| 31.09 | 2.87 | 3.1 |
| 31.36 | 2.85 | 0.8 |
| 31.98 | 2.80 | 2.2 |
| 32.23 | 2.78 | 1.7 |
| 32.37 | 2.76 | 0.6 |
| 32.64 | 2.74 | 1.5 |
| 33.03 | 2.71 | 0.1 |
| 33.34 | 2.69 | 1.0 |
| 33.47 | 2.68 | 1.3 |
| 34.08 | 2.63 | 0.7 |
| 34.55 | 2.59 | 1.8 |
| 34.73 | 2.58 | 0.4 |

[a] ± 0.1

After calcination, the X-ray powder diffraction pattern for SSZ-74 exhibits the characteristic lines shown in Table II below.

TABLE II

Calcined SSZ-74

| 2 Theta[(a)] | d-spacing (Angstroms) | Relative Integrated Intensity (%) |
|---|---|---|
| 7.98 | 11.07 | M |
| 8.70 | 10.16 | VS |
| 8.89 | 9.93 | S |
| 9.08 | 9.74 | S |
| 14.02 | 6.31 | W |
| 14.93 | 5.93 | M |
| 16.03 | 5.52 | M |
| 23.26 | 3.82 | VS |
| 23.95 | 3.71 | W |
| 24.08 | 3.69 | M |

[(a)] ± 0.1

Table IIA below shows the X-ray powder diffraction lines for calcined. SSZ-74 including actual relative intensities.

TABLE IIA

Calcined SSZ-74

| 2 Theta[(a)] | d-spacing (Angstroms) | Relative Integrated Intensity (%) |
|---|---|---|
| 7.98 | 11.07 | 34.9 |
| 8.70 | 10.16 | 86.8 |
| 8.89 | 9.93 | 40.2 |
| 9.08 | 9.74 | 47.0 |
| 9.66 | 9.15 | 1.0 |
| 11.26 | 7.85 | 0.4 |
| 11.34 | 7.80 | 0.5 |
| 12.76 | 6.93 | 1.1 |
| 13.26 | 6.67 | 4.6 |
| 14.02 | 6.31 | 13.4 |
| 14.93 | 5.93 | 20.9 |
| 16.03 | 5.52 | 23.5 |
| 16.39 | 5.40 | 4.3 |
| 16.61 | 5.33 | 4.4 |
| 17.12 | 5.18 | 3.0 |
| 17.80 | 4.98 | 2.8 |
| 18.19 | 4.87 | 7.6 |
| 19.05 | 4.66 | 1.9 |
| 19.74 | 4.49 | 0.4 |
| 20.44 | 4.34 | 3.0 |
| 20.75 | 4.28 | 3.4 |
| 21.19 | 4.19 | 7.7 |
| 21.67 | 4.10 | 4.1 |
| 21.99 | 4.04 | 5.8 |
| 22.68 | 3.92 | 3.7 |
| 22.79 | 3.90 | 9.5 |
| 23.26 | 3.82 | 100.0 |
| 23.95 | 3.71 | 14.2 |

[(a)] ± 0.1

The X-ray powder diffraction patterns were determined by standard techniques. The radiation was the K-alpha/doublet of copper. The peak heights and the positions, as a function of 2θ where θ is the Bragg angle, were read from the relative intensities of the peaks, and d, the interplanar spacing in Angstroms corresponding to the recorded lines, can be calculated.

The variation in the scattering angle (two theta) measurements, due to instrument error and to differences between individual samples, is estimated at ±0.1 degrees.

Representative peaks from the X-ray diffraction pattern of calcined SSZ-74 are shown in Table II. Calcination can result in changes in the intensities of the peaks as compared to patterns of the "as-made" material, as, well as minor shifts in the diffraction pattern.

Crystalline SSZ-74 can be used as-synthesized, but preferably will be thermally treated (calcined). Usually, it is desirable to remove the alkali metal cation (if any) by ion exchange and replace it with hydrogen, ammonium, or any desired metal ion.

SSZ-74 can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the SSZ-74 can be extruded before drying, or, dried or partially dried and then extruded.

SSZ-74 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

The molecular sieve of the present invention can be used in a catalysts to prepare methylamine or dimethylamine. Dimethylamine is generally prepared in industrial quantities by continuous reaction of methanol (and/or dimethylether) and ammonia in the presence of a silica-alumina catalyst. The reactants are typically combined in the vapor phase, at temperatures in the range of 300° C. to 500° C., and at elevated pressures. Such a process is disclosed in U.S. Pat. No. 4,737,592, issued Apr. 12, 1988 to Abrams et al., which is incorporated by reference in its entirety.

The catalyst is used in its acid form. Acid forms of molecular sieves can be prepared by a variety of techniques. Preferably, the molecular sieve used to prepare dimethylamine will be in the hydrogen form, or have an alkali or alkaline earth metal, such as Na, K, Rb, or Cs, ion-exchanged into it.

The process of the present invention involves reacting methanol, dimethylether or a mixture thereof and ammonia in amounts sufficient to provide a carbon/nitrogen (C/N) ratio from about 0.2 to about 1.5, preferably about 0.5 to about 1.2. The reaction is conducted at a temperature from about 250° C. to about 450° C., preferably about 300° C. to about 400° C. Reaction pressures can vary from about 7-700 kPa (1-1000 psi), preferably about 70-3000 kPa (10-500 psi). A methanol and/or dimethylether space time of about 0.01-80 hours, preferably 0.10-1.5 hours, is typically used. This space time is calculated as the mass of catalyst divided by the mass flow rate of methanol/dimethylether introduced into the reactor.

EXAMPLES

The following examples demonstrate but do not limit the present invention.

Example 1

Synthesis of Hexamethylene-1,6-bis-(N-methyl-N-pyrrolidinium)dication SDA

In 50 ml of acetone was dissolved 5 ml (48 mmoles) of N-methyl pyrrolidine. 4.9 Grams of 1,6 dibromohexane (20 mmoles) were added and the resulting mixture was stirred at room temperature for three days. Solids formed and were collected by filtration and washed with ether and kept in a vacuum oven. Then 3.71 grams of the dried solid was mixed into 18.7 grams of water and 9.57 grams of AG1-X8 resin for exchange to the OH form. The exchange was run overnight and then the solution was collected and titrated.

Example 2

Synthesis of All-Silica SSZ-74

6.4 Grams of the solution from Example 1 (3 mmoles) was mixed in a tared Teflon cup with 1.276 grams of tetraethyl orthosilicate and then allowed to evaporate (5 in a hood) for several days as hydrolysis occurred. A second reaction was set up the same way. After evaporation to the appearance of dryness, one reaction was given 0.20 gram of water and mixed. The second was given 0.60 gram of water and the same treatment ensued. 0.125 Gram of about 50% HF was carefully added to each reaction mixture and the contents were stirred with a plastic spatula and a thick gel formed. In the first case the H2O/SiO2 ratio was now roughly 3.5 and it was 7.0 in the second case. The materials were heated to 150° C. and at 43 RPM in tumbled Parr reactors placed in a Blue M convection heating oven. The reactions were cooled and opened in 6 day periods with a small amount examined by Scanning Electron Microscopy to determine if crystals had formed. After 22 days there was crystalline material in both and the solids were collected (filtration) and washed with copious amounts of water, air dried and then examined by X-ray diffraction (XRD). The product in both cases was SSZ-74.

Example 3

Calcination of SSZ-74

The products from both reactions in Example 2 were calcined in stages and in air to 595° C. to remove the organic content. The materials were found to be stable and the XRD patterns showed the relationship to the as-made SSZ-74.

Example 4

Adsorption of 2,2-Dimethylbutane

The calcined material of Example 3 was then tested for the uptake of the hydrocarbon 2,2-dimethylbutane. This adsorbate does not enter small pore zeolites (8-ring portals) and sometimes is hindered in entering intermediate pore zeolites like ZSM-5. The SSZ-74 showed a profile more characteristic of intermediated pore materials (as contrasted to Y zeolite, a large pore material), showing steady gradual uptake of the adsorbate.

SSZ-74 was shown to adsorb about 0.08 cc/gram after 3 hours of exposure to the 2,2 dimethyl butane adsorbate using a pulsed mode. This value compares with an analysis for ZSM-5 zeolite which gives a value closer to 0.07 cc/gm at the same point in time under the same experimental conditions. This would indicate that the pores of SSZ-74 are at least 10-rings

Example 5

2-6 Synthesis of Aluminosilicate SSZ-74

The synthesis parameters of Example 2 were repeated except for the following changes. (1) 0.04 gram of Y zeolite material LZ-210 was added as a potential contributor of Al; (2) the initial H2O/SiO2 ratio for the synthesis was adjusted to 5; (3) seeds of a successful SSZ-74 product were added; and (4) the reaction was run at 170° C. After 9 days there was crystalline material which was SSZ-74 when worked up and analyzed by XRD. The solids were calcined then as in Example 3.

Example 6

Constraint Index 0.12 grams of the material from Example 5, in a 20-40 pelleted and meshed range, was loaded into a stainless steel reactor and run in a Constraint Index test (50/50 n-hexane/3-methylpentane). The normal feed rate was used (8 µl/min.) and the test was run at 700° F. after the catalyst had been dried in the reactor to near 1000° F. Helium flow was used. At 10 minutes on-stream nearly 30% of the feed was being converted with about equal amounts of each reactant. The selectivity did not change as the catalyst fouled to half the conversion at 100 minutes. The pores of the active SSZ-74 were at least intermediate in size.

Example 7

Synthesis of Aluminosilicate SSZ-74

Three mMoles of SDA solution and 1.26 grams (6 mmoles) of tetraethylorthosilicate were combined in a Teflon cup for a Parr reactor. The contents were allowed to react and then most of the water and then the ethanol by-product were allowed to evaporate in a hood over several days. Once the H2O(SiO2 ratio was about 5, from the evaporation, 0.04 grams of LZ-210 zeolite were added (LZ-210 is a Y zeolite which has been treated with $(NH_4^+)_2SiF_6$ to provide some de-alumination). A few mg of seeds of SSZ-74 were added in the as-made state. Lastly, 0.132 gram of 50% HF was added and the reactor was closed up and heated at 170° C., 43 RPM, for six days. A sample of the cooled reaction product showed nicely crystalline maternal in an electron microscope. The reaction contents were worked up and dried. Analysis by X-ray diffraction showed the product to be molecular sieve SSZ-74.

The sample was calcined (in air to 595° C.) and then pelleted and meshed (20-40) and run in a standard Constraint Index test. At 700° F. the initial conversion was 28% with a CI value of 1.1. With time-on-stream the catalyst showed a steady deactivation while the CI value did not change much.

What is claimed is:

1. A process for producing methylamine or dimethylamine comprising reacting methanol, dimethyl ether or a mixture thereof and ammonia in the gaseous phase in the presence of a catalyst comprising a crystalline molecular sieve having a mole ratio greater than about 15 of (1) an oxide of a first tetravalent element to (2) an oxide of a trivalent element, pentavalent element, second tetravalent element which is different from said first tetravalent element or mixture thereof and having, after calcination, the X-ray diffraction lines of Table II, as follows:

TABLE II

Calcined SSZ-74

| 2 Theta[a] | d-spacing (Angstroms) | Relative Integrated Intensity (%) |
|---|---|---|
| 7.98 | 11.07 | M |
| 8.70 | 10.16 | VS |
| 8.89 | 9.93 | S |
| 9.08 | 9.74 | S |
| 14.02 | 6.31 | W |
| 14.93 | 5.93 | M |
| 16.03 | 5.52 | M |

TABLE II-continued

Calcined SSZ-74

| 2 Theta$^a$ | d-spacing (Angstroms) | Relative Integrated Intensity (%) |
|---|---|---|
| 23.26 | 3.82 | VS |
| 23.95 | 3.71 | W |
| 24.08 | 3.69 | M |

$^a$±0.1.

2. The process of claim 1 wherein the molecular sieve has a mole ratio greater than about 15 of (1) silicon oxide to (2) an oxide selected from aluminum oxide, gallium oxide, iron oxide, boron oxide, titanium oxide, indium oxide and mixtures thereof.

3. The process of claim 1 or 2 wherein the methanol, dimethylether or mixture thereof and ammonia are present in amounts sufficient to provide a carbon/nitrogen ratio from about 0.2 to about 1.5.

4. The process of claim 1 or 2 conducted at a temperature of from about 250° C. to about 450° C.

* * * * *